United States Patent
Wu et al.

(10) Patent No.: US 10,569,282 B2
(45) Date of Patent: Feb. 25, 2020

(54) LIGHT SOURCE MODULE AND MICROPARTICLES SORTING APPARATUS HAVING THE SAME

(71) Applicant: TECHTRON TECHNOLOGY CO., LTD., New Taipei (TW)

(72) Inventors: Hung-Wei Wu, Tainan (TW); Cheng-Yuan Hung, Kaohsiung (TW); Chang-Sin Ye, Tainan (TW)

(73) Assignee: TECHTRON TECHNOLOGY CO., LTD., New Taipei (TW)

( * ) Notice: Subject to any disclaimer, the term of this patent is extended or adjusted under 35 U.S.C. 154(b) by 377 days.

(21) Appl. No.: 15/491,993

(22) Filed: Apr. 20, 2017

(65) Prior Publication Data

US 2018/0117599 A1    May 3, 2018

(30) Foreign Application Priority Data

Oct. 27, 2016   (TW) .............................. 105134721 A

(51) Int. Cl.
| | |
|---|---|
| *G01N 15/02* | (2006.01) |
| *B03C 5/02* | (2006.01) |
| *B01L 3/00* | (2006.01) |
| *G09G 3/00* | (2006.01) |
| *B03C 5/00* | (2006.01) |
| *G02B 27/00* | (2006.01) |

(52) U.S. Cl.
CPC ........ *B03C 5/022* (2013.01); *B01L 3/502761* (2013.01); *G09G 3/002* (2013.01); *B01L 2200/0652* (2013.01); *B01L 2300/0654* (2013.01); *B01L 2400/0424* (2013.01); *B01L 2400/0454* (2013.01); *B03C 5/005* (2013.01); *G01N 15/0266* (2013.01); *G02B 27/0018* (2013.01)

(58) Field of Classification Search
CPC ........... G01N 15/0205; G01N 15/0227; G01N 15/02; G01N 15/0211; G01N 15/147
USPC ....................................................... 356/335
See application file for complete search history.

(56) References Cited

U.S. PATENT DOCUMENTS

| | | | |
|---|---|---|---|
| 7,690,797 B2 † | 4/2010 | Higashi | |
| RE44,711 E † | 1/2014 | Wu | |
| 2006/0238716 A1* | 10/2006 | Lee | G02B 27/102 353/20 |
| 2009/0170186 A1* | 7/2009 | Wu | B03C 5/026 435/286.1 |

(Continued)

FOREIGN PATENT DOCUMENTS

| | | |
|---|---|---|
| CN | 102449163 A | 5/2012 |

*Primary Examiner* — Md M Rahman
(74) *Attorney, Agent, or Firm* — CKC & Partners Co., LLC

(57) ABSTRACT

A light source module for microparticles sorting performed in a light-induced dielectrophoresis chip is provided, which includes a light emitting element, a control unit and a light converting unit. The light emitting element is configured to generate and emit light. The control unit is configured to generate a driving signal based on image data. The Light converting unit is coupled to the control unit, and is configured to convert the light into a light pattern based on the driving signal. A luminous exitance of the light converting unit is between $9 \times 10^4$ lux and $1.2 \times 10^5$ lux.

17 Claims, 4 Drawing Sheets

(56) References Cited

U.S. PATENT DOCUMENTS

| | | | |
|---|---|---|---|
| 2012/0118740 A1* | 5/2012 | Garcia | B03C 5/005 |
| | | | 204/547 |
| 2012/0249829 A1* | 10/2012 | Izuha | H01L 27/14621 |
| | | | 348/229.1 |
| 2013/0021407 A1* | 1/2013 | Maida | B41J 2/16535 |
| | | | 347/28 |
| 2013/0120718 A1* | 5/2013 | Chikaoka | G02B 26/101 |
| | | | 353/85 |
| 2013/0335642 A1† | 12/2013 | Fujioka | |
| 2014/0124373 A1 | 5/2014 | Chen et al. | |
| 2014/0153238 A1* | 6/2014 | Nishimura | H01L 25/0753 |
| | | | 362/237 |
| 2015/0178412 A1* | 6/2015 | Grau | G06F 17/50 |
| | | | 703/1 |
| 2015/0221623 A1* | 8/2015 | Tischler | H01L 25/165 |
| | | | 257/89 |
| 2015/0377445 A1* | 12/2015 | Chuang | B60Q 1/143 |
| | | | 362/465 |

\* cited by examiner
† cited by third party

LIGHT SOURCE MODULE AND MICROPARTICLES SORTING APPARATUS HAVING THE SAME

RELATED APPLICATIONS

This application claims priority to Taiwan Patent Application Serial Number 105134721, filed on Oct. 27, 2016, which is herein incorporated by reference.

BACKGROUND

Field of the Invention

The invention relates to a light source module or microparticles sorting, and more particularly to a light source module for microparticles sorting using light-induced dielectrophoresis (LIDEP) theory and a microparticles sorting apparatus having the same.

Description of Related Art

Medical examination is e method of performing analyses on microparticles or molecules by utilizing various medical analysis instruments and assisting an evaluation of an organism's physical condition based on analyzing results. If only one type of microparticles is to be analyzed, a sorting process needs to be performed on different microparticles in a fluid. In recent years, a technology which applies light-induced dielectrophoresis (LIDEP) theory for microparticles sorting has been developed. However, factors such as chip design, operating environment and light source affects the efficiency of microparticles sorting using LIDEP theory.

SUMMARY OF THE INVENTION

An objective of the invention is to provide a light source module and a microparticles sorting apparatus having the same for high-purity microparticles sorting using light-induced dielectrophoresis (LIDEP) theory.

One aspect of the invention is directed to a light source module for microparticles sorting performed in a light-induced dielectrophoresis chip. The light source module includes a light emitting element, a control unit and a light converting unit. The light emitting element is configured to generate and emit light. The control unit is configured to generate a driving signal based on image data. The light converting unit is coupled to the control unit, and is configured to convert the light into a light pattern based on the driving signal. A luminous exitance of the light converting unit is between $9 \times 10^4$ lux and $1.2 \times 10^5$ lux.

In accordance with some embodiments of the invention, the light pattern is a grayscale light pattern.

In accordance with some embodiments of the invention, a contrast ration of the light pattern is between $10^3:1$ and $1.5 \times 10^5:1$.

In accordance with some embodiments of the invention, the light emitting element comprises a white light emitting diode, and the light is visible light.

In accordance with some embodiments of the invention, a wavelength of the light pattern is substantially in a range between 280 nm and 1400 nm.

In accordance with some embodiments of the invention, the light converting unit comprises a digital micro or device (DMD).

In accordance with some embodiments of the invention, the light, converting unit comprises a liquid crystal on silicon (LCoS) device.

In accordance with some embodiments of the invention, the light source module further includes a communication unit. The communication unit is coupled to the control unit, and is configured to communicatively connect with a computer device and to receive the image data from the computer device.

In accordance with some embodiments of the invention, the light source module further includes a lens unit and a connection unit. The lens unit is configured to adjust a planar size of the light pattern. The connection unit having opposite first and second terminals, wherein the first terminal is at a light penetrating side of the light converting unit, and the second terminal is configured to accommodate the lens unit.

In accordance with some embodiments of the invention, the connection unit is a retractable cylindrical structure.

In accordance with some embodiments of the invention, a maximum extending length of the connection unit is about 30 cm.

In accordance with some embodiments of the invention, a focusing range of the light pattern is between 10 cm and 30 cm.

Another aspect of the invention is directed to a microparticles sorting apparatus, which includes a light-induced dielectrophoresis chip and a light perform microparticles sorting under illumination of a light pattern. The light source module configured to provide the light pattern for the light-induced dielectrophoresis chip. The light source module includes a fight emitting element, a control unit and a light converting unit. The light emitting element is configured to generate and emit light. The control unit is configured to generate a driving signal based on image data. The light converting unit is coupled to the control unit, and is configured to convert the light into the light pattern based on the driving signal. A luminous exitance of the light converting unit is between $9 \times 10^4$ lux and $1.2 \times 10^5$ lux.

BRIEF DESCRIPTION OF THE DRAWINGS

The foregoing aspects and many of the accompanying advantages of this invention will become more readily appreciated as the same becomes better understood by reference to the following detailed description, when taken in conjunction with the accompanying drawings.

DETAILED DESCRIPTION OF THE INVENTION

The detailed explanation of the present invention is described as following. The described preferred embodiments are presented for purposes of illustrations and description, and they are not intended to limit the scope of the present invention.

Figure 1:
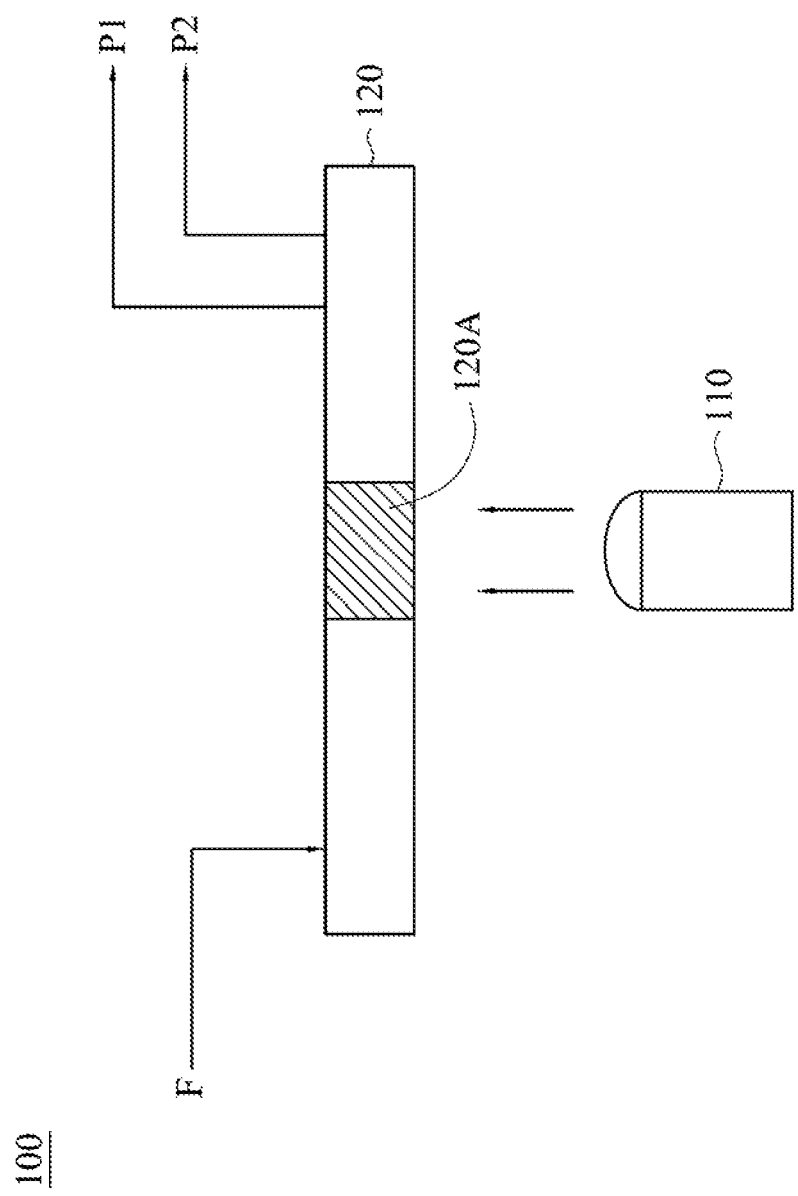
FIG. 1 illustrates a schematic diagram of a microparticles sorting apparatus in accordance with some embodiments of the invention.

Referring to FIG. 1, FIG. 1 illustrates a schematic diagram of a microparticles sorting apparatus 100 in accordance with some embodiments of the invention. The microparticles sorting apparatus 100 includes a light source module 110 and a light-induced dielectrophoresis chip 120. The light source module 110 is configured to generate a light pattern, and the light-induced dielectrophoresis chip 120 is configured to performing a sorting process on different microparticles under the illumination of the light pattern. The light pattern may be a color light pattern or a grayscale light pattern, and the contrast ratio thereof is in a range between $10^3:1$ and $1.5\times10^5:1$. In the context, the microparticles may be biological cells, air particles, waterborne impurities or dielectric powders. For example, a fluid F which includes first microparticles P1 and second microparticles P2 is injected into the light-induced dielectrophoresis chip 120, and the light-induced dielectrophoresis chip 120 may produce a non-uniform electric field at its projection area 120A by the effect of the light pattern, so as to produce a resistance difference in the light-induced dielectrophoresis chip 120, such that the surfaces of the first microparticles P1 and the second, microparticles P2 accumulate electric charges of different densities, thereby moving to different locations by different dielectrophoresis forces. As such, the first microparticles P1 and the second microparticles P2 in the fluid F can be sorted out by the light-induced dielectrophoresis chip 120.

Figure 2:
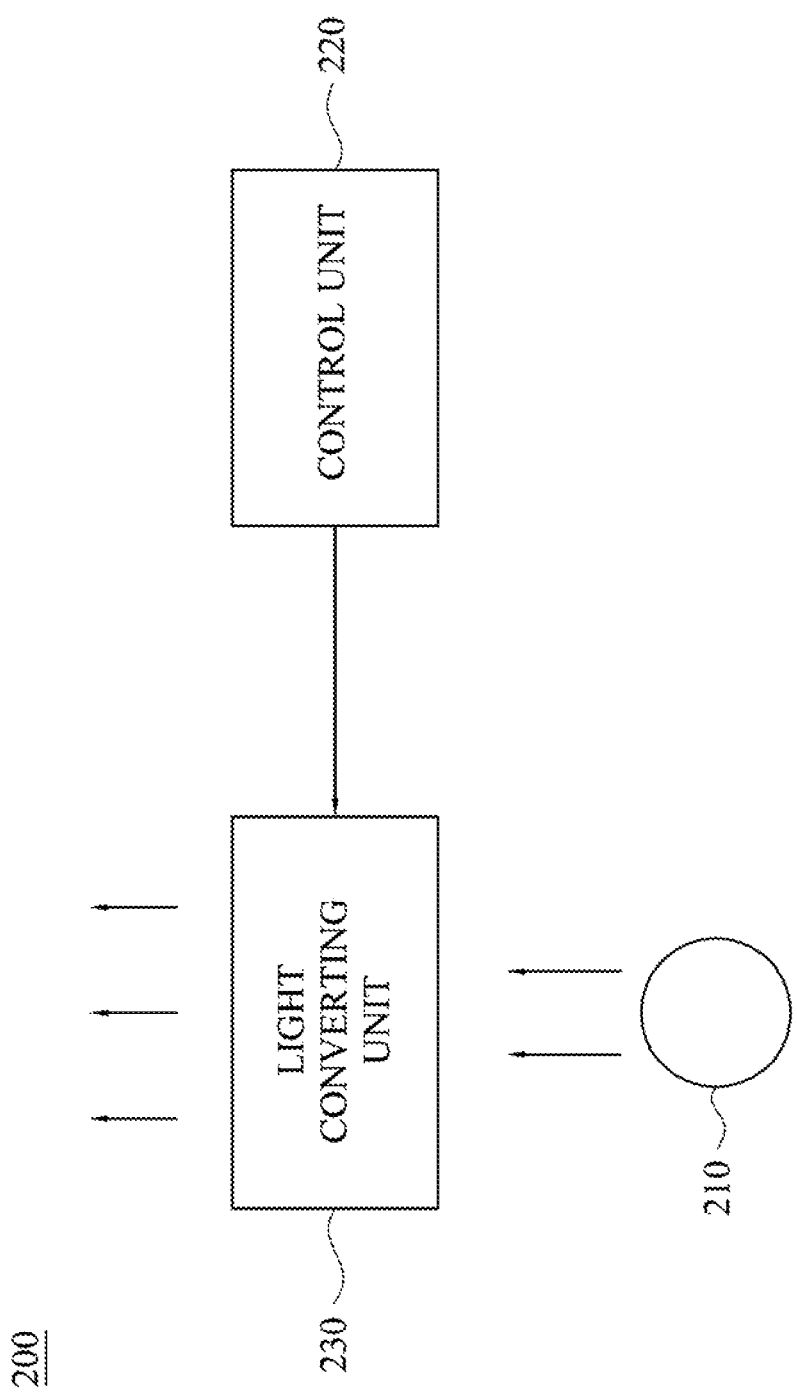
FIG. 2 illustrates a schematic diagram of a light source module in accordance with some embodiments of the invention.

FIG. 2 illustrates a schematic diagram of a light source module 200 in accordance with some embodiments of the invention. The light source module 200 may be, for example, the light source module 110 of FIG. 1, and includes a light emitting element 210, a control unit 220 and a light converting unit 230. The light emitting element 210 is configured to generate light, and may be, for example, a lamp, a light emitting diode or a laser, but is not limited thereto. For example, the light emitting element 210 may be a light emitting diode which is configured to emit light including a wavelength range of visible light. The control unit 220 is configured to generate a driving signal based on the image data, and to transmit the driving signal to the light converting unit 230, such that the light converting unit 230 converts the light emitted by the light emitting element 210 into a light pattern accordingly. In order to achieve optimum microparticles sorting performance, the luminous exitance of the light converting unit 230 may be between $9\times10^4$ lux and $1.2\times10^5$ lux, and the wavelength of the generated light pattern may be in a range between 280 nm and 1400 nm. The light converting unit 230 may include a digital micromirror device (DMD) or a liquid crystal on silicon (LCoS) device, and may determine the light pattern to be outputted based on the driving signal. The resolution and the number of distinct colors of the light pattern may be 1920×1080 pixels and 16 million colors (e.g. 16.7 million colors or 16.2 million colors), respectively, but are not limited thereto. For example, in some embodiments, the light pattern generated by the light converting unit 230 may be 640×480 pixels and 256 grayscale levels. In addition, in further some embodiments, the light pattern generated by the light converting unit 230 may be analog. On the other hand the image data may correspond to dynamic image data, such that the light converting unit 230 dynamically adjusts the light pattern based on the driving signal.

Figure 3:
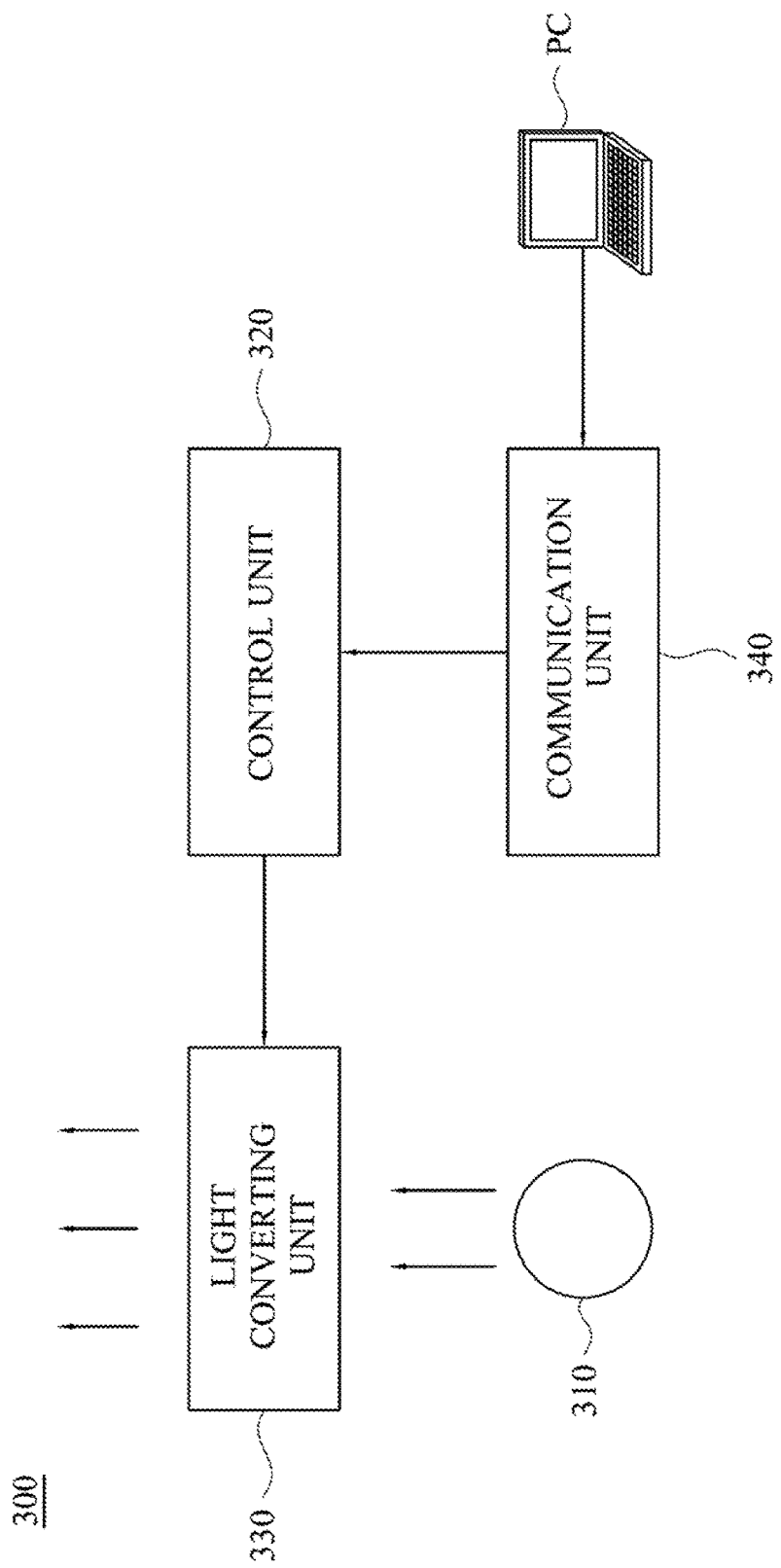
FIG. 3 illustrates a schematic diagram of a light source module in accordance with other some embodiments of the invention.

FIG. 3 illustrates a schematic diagram of a light source module 300 in accordance with other some embodiments of the invention. The light source module 300 may be, for example, the light source module 110 of FIG. 1, and includes a light emitting element 310, a control unit 320, a light converting unit 330 and a communication unit 340. The difference between the light source module 300 and the light source module 200 of FIG. 2 is that the light source module 300 further includes the communication unit 340, which is configured to communicatively connect with the computer device PC and to receive the image data from the computer device PC. In detail, the communication unit 340 may use a wired communication (such as VGA, HDMI, eDP and USB) or wireless communication (such as WiFi and Bluetooth) mechanism to communicatively connect with the computer device PC, and the computer device PC transmits the image data to the communication unit 340, and then the control unit 320 generates the driving signal based on the received image data and transmits the driving signal to the light converting unit 330, such that the light converting unit 330 converts the light emitted by the light emitting element 310 into the light pattern accordingly. The light emitting element 310 and the light converting unit 330 are similar to the light emitting element 210 and the light converting unit 230 of FIG. 2, respectively, and the related descriptions thereof can refer to the foregoing paragraphs and therefore will not be repeated herein.

Figure 4:
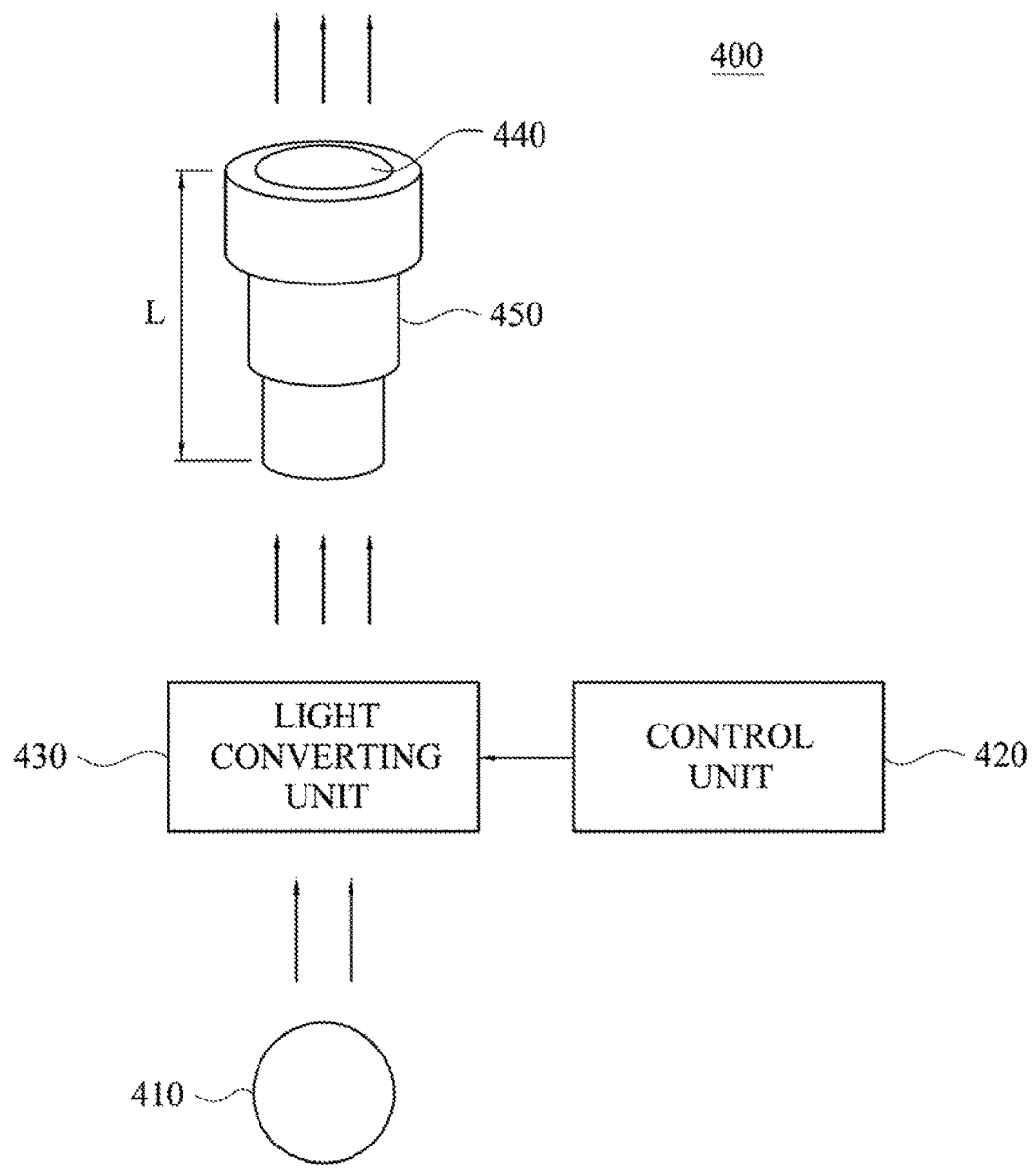
FIG. 4 illustrates a schematic diagram of a light source module in accordance with further some embodiments of the invention.

FIG. 4 illustrates a schematic diagram of the light source module 400 in accordance with further some embodiments of the invention. The light source module 400 may be, for example, the light source module 110 of FIG. 1 and includes a light emitting element 410, a control unit 420, a light converting unit 430, a lens unit 440 and a connection unit 450. The difference between the light source module 400 and, the light source module 200 of FIG. 2 is that the light source module 400 further includes the lens unit 440 and the connection unit 450. The lens unit 440 is configured to adjust the planar size of the light pattern emitted by light converting unit 430. The connection unit 450 is a cylindrical structure, the first terminal of which is located at the light penetrating side of the light converting unit 430, and the second terminal thereof is configured accommodate the lens unit 440. The magnification of the lens unit 440 may be ¼ to ½, but is not limited thereto. The connection unit 450 may be a retractable cylindrical structure, which is adapted to extend the object distance, so as to shorten the projection distance of the light source module 400 and to avoid optical loss due to light pattern leakage. With the disposal of the lens unit 440 and the connection unit 450, the focusing range of the light pattern may be between 10 cm and 30 cm. Further, the focusing range of the light pattern is preferably about 20 cm. In some embodiments, the maximum extending length of the connection unit 450 is about 30 cm. The light emitting element 410 and the light converting unit 430 are similar to the light emitting element and the light converting unit 230 of FIG. 2, respectively. In addition, the light source module 400 may further includes a communication unit (not shown in FIG. 4), and such communication unit (not shown in FIG. 4) and the control unit 420 are similar to the communication unit 340 and the control unit 320, respectively. The related descriptions of the light emitting element 410, the control unit 420 and the light converting unit 430 can refer to the foregoing paragraphs and therefore will not be repeated herein.

With the light pattern generated by the light source module of the invention, the internal electric field of alight-induced dielectrophoresis chip can be accurately changed, thereby sorting out microparticles with high purity. Therefore, the light source module of the invention is suitable for biological and medical applications, such as biochemical treatment and laboratory medicine.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims.

What is claimed is:

1. A light source module for microparticles sorting performed in a light-induced dielectrophoresis chip, the light source module comprising:
   a light emitting element configured to generate and emit light;
   a controller configured to generate a driving signal based on image data;
   a light converter coupled to the controller, the light converter configured to convert the light into a light pattern based on the driving signal, and a luminous exitance of the light converter is between $9\times10^4$ lux and $1.2\times10^5$ lux;
   a lens configured to adjust a planar size of the light pattern; and
   a retractable cylindrical structure having opposite first and second terminals, wherein the first terminal of the retractable cylindrical structure is at a light penetrating side of the light converter, and the second terminal of the retractable cylindrical structure is configured to accommodate the lens.

2. The light source module of claim 1, wherein the light pattern is a grayscale light pattern.

3. The light source module of claim 1, wherein a contrast ration of the light pattern is between $10^3$:1 and $1.5\times10^5$:1.

4. The light source module of claim 1, wherein the light emitting element comprises a white light emitting diode, and the light is visible light.

5. The light source module of claim 1, wherein a wavelength of the light pattern is substantially in a range between 280 nm and 1400 nm.

6. The light source module of claim 1, wherein the light converter comprises a digital micromirror device (DMD).

7. The light source module of claim 1, wherein the light converter comprises a liquid crystal on silicon (LCoS) device.

8. The light source module of claim 1, further comprising:
   a communicator coupled to the controller, the controller configured to communicatively connect with a computer device and to receive the image data from the computer device.

9. The light source module of claim 1, wherein a maximum extending length of the retractable cylindrical structure is about 30 cm.

10. The light source module of claim 1, wherein a focusing range of the light pattern is between 10 cm and 30 cm.

11. A microparticles sorting apparatus, comprising:
    a light-induced dielectrophoresis chip configured to perform microparticles sorting under illumination of a light pattern;
    a light source module configured to provide the light pattern for the light-induced dielectrophoresis chip, the light source module comprising:
       a light emitting element configured to generate and emit light;
       a controller configured to generate a driving signal based on image data; and
       a light converter coupled to the controller, the light converter configured to convert the light into the light pattern based on the driving signal, and a luminous exitance of the light converter is between $9\times10^4$ lux and $1.2\times10^5$ lux;
    a lens configured to adjust a planar size of the light pattern; and
    a retractable cylindrical structure having opposite first and second terminals, wherein the first terminal of the retractable cylindrical structure is at a light penetrating side of the light converter, and the second terminal of the retractable cylindrical structure is configured to accommodate the lens.

12. The microparticles sorting apparatus of claim 11, wherein the light pattern is a grayscale light pattern.

13. The microparticles sorting apparatus of claim 11, wherein a contrast ration of the light pattern is between $10^3$:1 and $1.5\times10^5$:1.

14. The microparticles sorting apparatus of claim 11, wherein the light emitting element comprises a white light emitting diode, and the light is visible light.

15. The microparticles sorting apparatus of claim 11, wherein a wavelength of the light pattern is substantially in a range between 280 nm and 1400 nm.

16. The microparticles sorting apparatus of claim 11, wherein the light converter comprises a digital micromirror device (DMD) or a liquid crystal on silicon (LCoS) device.

17. The microparticles sorting apparatus of claim 11, further comprising:
    a communicator coupled to the controller, the communicator configured to communicatively connect with a computer device and to receive the image data from the computer device.

* * * * *